US009383220B2

(12) United States Patent
Crankson et al.

(10) Patent No.: US 9,383,220 B2
(45) Date of Patent: Jul. 5, 2016

(54) ACTIVITY IDENTIFICATION (71) Applicant: NIKE, Inc., Beaverton, OR (US)

(72) Inventors: Kwamina Crankson, Portland, OR (US); Michael Schmitt, Portland, OR (US); Aaron B Weast, Portland, OR (US)

(73) Assignee: NIKE, Inc., Beaverton, OR (US)

( * ) Notice: Subject to any disclaimer, the term of this patent is extended or adjusted under 35 U.S.C. 154(b) by 0 days.

(21) Appl. No.: 13/743,916

(22) Filed: Jan. 17, 2013

(65) Prior Publication Data

US 2013/0132028 A1    May 23, 2013

Related U.S. Application Data (63) Continuation-in-part of application No. 13/287,064, filed on Nov. 1, 2011, which is a continuation-in-part of application No. 13/068,870, filed on Nov. 1, 2010, now abandoned, application No. 13/743,916, which is a continuation-in-part of application No. 13/353,267, filed on Jan. 18, 2012, now Pat. No. 8,974,349.

(60) Provisional application No. 61/588,012, filed on Jan. 18, 2012.

(51) Int. Cl.
*A63B 24/00* (2006.01)
*G01C 22/00* (2006.01)
*G06F 19/00* (2011.01)
*G09B 19/00* (2006.01)
*H04M 1/725* (2006.01)

(52) U.S. Cl.
CPC .......... *G01C 22/006* (2013.01); *G06F 19/3481* (2013.01); *G09B 19/0038* (2013.01); *H04M 1/7253* (2013.01); *H04M 2250/12* (2013.01)

(58) Field of Classification Search
CPC ........................... A63B 24/00; A63B 24/0062
USPC .............................................. 482/1, 8; 700/91
See application file for complete search history.

(56) References Cited

U.S. PATENT DOCUMENTS

| 1,093,757 A | 4/1914 | Becken |
| 3,113,362 A | 12/1963 | Petruzziello |
| 3,838,568 A | 10/1974 | Zurcher et al. |

(Continued)

FOREIGN PATENT DOCUMENTS

| CN | 1425356 A | 6/2003 |
| CN | 101242880 A | 8/2008 |

(Continued)

OTHER PUBLICATIONS

Partial European Search Report for related application No. 13150151.2 mailed May 31, 2013.

(Continued)

*Primary Examiner* — Allen Chan
(74) *Attorney, Agent, or Firm* — Banner & Witcoff, Ltd.

(57) ABSTRACT

Systems and method for calculating energy expenditure values and activity points are provided. One or more devices may use an accelerometer and/or other sensors to monitor activity of a user. The user may identify the activity via one of the devices, a mobile phone, a computer device or another device. Activity points or energy expenditure values may be calculated from data received from sensors and the identification provided by the user.

20 Claims, 6 Drawing Sheets

(56) References Cited

U.S. PATENT DOCUMENTS

| | | | |
|---|---|---|---|
| 3,971,206 A | 7/1976 | Martino | |
| 3,992,870 A | 11/1976 | Dekel | |
| 4,121,415 A | 10/1978 | Crutcher et al. | |
| 6,278,378 B1 | 8/2001 | Feiner et al. | |
| 6,435,709 B2 | 8/2002 | Hirano et al. | |
| 6,505,763 B2 | 1/2003 | Rota | |
| 6,513,532 B2 | 2/2003 | Mault et al. | |
| 6,604,419 B2 | 8/2003 | Guzman | |
| 7,402,125 B2 | 7/2008 | Wang | |
| 7,470,234 B1 | 12/2008 | Elhag et al. | |
| 7,618,260 B2 | 11/2009 | Daniel et al. | |
| 7,645,211 B1 | 1/2010 | Thomeczek et al. | |
| 7,710,262 B2 | 5/2010 | Ruha | |
| 7,892,145 B2 | 2/2011 | Lovett et al. | |
| 7,955,219 B2 | 6/2011 | Birrell et al. | |
| 7,972,245 B2 | 7/2011 | Temple et al. | |
| 8,040,758 B1 | 10/2011 | Dickinson | |
| 8,105,208 B2 | 1/2012 | Oleson et al. | |
| 8,248,247 B2 | 8/2012 | Boyd et al. | |
| 8,328,694 B2 | 12/2012 | Barre et al. | |
| 8,469,862 B2 | 6/2013 | Andren et al. | |
| 8,515,505 B1 | 8/2013 | Pattikonda | |
| 8,562,489 B2 | 10/2013 | Burton et al. | |
| 8,620,617 B2 | 12/2013 | Yuen et al. | |
| 8,690,736 B2 | 4/2014 | Napolitano et al. | |
| 8,825,445 B2 | 9/2014 | Hoffman et al. | |
| 8,879,368 B2 | 11/2014 | Jacobi, Jr. | |
| 8,956,290 B2 | 2/2015 | Gilley et al. | |
| 2002/0109600 A1 | 8/2002 | Mault et al. | |
| 2004/0131997 A1 | 7/2004 | McGuire et al. | |
| 2005/0113650 A1 | 5/2005 | Pacione et al. | |
| 2005/0171410 A1 | 8/2005 | Hjelt et al. | |
| 2005/0189906 A1 | 9/2005 | Sun | |
| 2005/0202934 A1* | 9/2005 | Olrik et al. | 482/8 |
| 2005/0283051 A1 | 12/2005 | Chen | |
| 2006/0109645 A1 | 5/2006 | Ferrari et al. | |
| 2006/0198120 A1 | 9/2006 | Guzman | |
| 2006/0268007 A1 | 11/2006 | Gopalakrishnan | |
| 2007/0197274 A1 | 8/2007 | Dugan | |
| 2007/0287596 A1* | 12/2007 | Case et al. | 482/8 |
| 2008/0096726 A1* | 4/2008 | Riley et al. | 482/8 |
| 2008/0125288 A1 | 5/2008 | Case | |
| 2008/0153670 A1 | 6/2008 | McKirdy et al. | |
| 2008/0171635 A1 | 7/2008 | Yoshida et al. | |
| 2008/0171636 A1 | 7/2008 | Usui et al. | |
| 2008/0243038 A1 | 10/2008 | Bennett | |
| 2009/0005220 A1* | 1/2009 | Lee et al. | 482/8 |
| 2009/0059730 A1 | 3/2009 | Lyons et al. | |
| 2009/0093341 A1 | 4/2009 | James et al. | |
| 2009/0138636 A1 | 5/2009 | Burton et al. | |
| 2009/0144639 A1 | 6/2009 | Nims et al. | |
| 2009/0298649 A1* | 12/2009 | Dyer et al. | 482/4 |
| 2009/0298650 A1 | 12/2009 | Kutliroff | |
| 2010/0056340 A1 | 3/2010 | Ellis et al. | |
| 2010/0056341 A1 | 3/2010 | Ellis et al. | |
| 2010/0069203 A1* | 3/2010 | Kawaguchi et al. | 482/8 |
| 2010/0076331 A1 | 3/2010 | Chan et al. | |
| 2010/0292599 A1 | 11/2010 | Oleson et al. | |
| 2011/0130247 A1 | 6/2011 | Lovett et al. | |

FOREIGN PATENT DOCUMENTS

| | | | |
|---|---|---|---|
| CN | 101520815 A | 9/2009 | |
| EP | 1178374 A2 | 2/2002 | |
| EP | 2172249 A2 | 4/2010 | |
| JP | H10-113343 A | 5/1998 | |
| JP | H11-178967 A | 7/1999 | |
| JP | 2001202178 A | 7/2001 | |
| JP | 2001-284835 A | 10/2001 | |
| JP | 2002330933 A | 11/2002 | |
| JP | 2004500949 A | 1/2004 | |
| JP | 2006-200909 A | 8/2006 | |
| JP | 2006218246 A | 8/2006 | |
| JP | 2009-536041 A | 10/2009 | |
| JP | 2010017525 A | 1/2010 | |
| JP | 2010264247 A | 11/2010 | |
| JP | 2011045524 A | 3/2011 | |
| KR | 100758701 B1 | 9/2007 | |
| KR | 20100032076 A | 3/2010 | |
| WO | 2004073494 A2 | 9/2004 | |
| WO | 2007137264 A2 | 11/2007 | |
| WO | 2009/039313 A1 | 3/2009 | |
| WO | 2009124193 A1 | 10/2009 | |

OTHER PUBLICATIONS

Search Report and Written Opinion for international application No. PCT/US2013/021655 mailed Aug. 12, 2013.

Garmin, "Garmin Forerunner 405—Simple Workouts", Oct. 23, 2008, XP002669947, Retrieved from the Internet from <http://www.youtube.com/watch?v=Cnx9kQQpKv4>, the part of the video between 00:25 and 01:10.

International Search Report dated Jun. 22, 2012, PCT/US2011/058852, filed Nov. 1, 2011.

International Search Report and Written Opinion for application No. PCT/US2011/058849 dated Jun. 22, 2012.

Minamikawa, Atsunori, and 2 others, Energy Expenditure Monitoring System on Mobile Phone Using Information Gain Based Locomotion Estimation Method, Transactions of Information Processing Society of Japan, Transactions Journal, Japan, Information Processing Society of Japan, Jan. 15, 2011, vol. 52, No. 2, pp. 866 to 876.

* cited by examiner

ACTIVITY IDENTIFICATION

This application is a continuation-in-part application of application Ser. No. 13/287,064, filed Nov. 1, 2011 which is a continuation-in-part of application Ser. No. 13/068,870, filed Nov. 1, 2010. This application is also a continuation-in-part application of application Ser. No. 13/353,267, filed Jan. 18, 2012, and claims priority to U.S. Provisional Application No. 61/588,012, filed Jan. 18, 2012. All of the above applications are incorporated herein by reference in their entireties.

BACKGROUND

While most people appreciate the importance of physical fitness, many have difficulty finding the motivation required to maintain a regular exercise program. Some people find it particularly difficult to maintain an exercise regimen that involves continuously repetitive motions, such as running, walking and bicycling.

Additionally, individuals may view exercise as work or a chore and thus, separate it from enjoyable aspects of their daily lives. Often, this clear separation between athletic activity and other activities reduces the amount of motivation that an individual might have toward exercising. Further, athletic activity services and systems directed toward encouraging individuals to engage in athletic activities might also be too focused on one or more particular activities while an individual's interests are ignored. This may further decrease a user's interest in participating in athletic activities or using the athletic activity services and systems.

Therefore, improved systems and methods to address these and other shortcomings in the art are desired.

BRIEF SUMMARY

The following presents a simplified summary in order to provide a basic understanding of some aspects of the invention. The summary is not an extensive overview of the invention. The following summary merely presents some concepts of the invention in a simplified form as a prelude to the description below.

Aspects of the invention relate to calculating activity points or energy expenditure values. In certain embodiments, one or more devices may use an accelerometer and/or other sensors to monitor activity of a user. The user may identify the activity via one of the devices, a mobile phone, a computer device or another device. Activity points or energy expenditure values may be calculated from data received from sensors and the identification provided by the user.

In some embodiments, the present invention can be partially or wholly implemented on a computer-readable medium, for example, by storing computer-executable instructions or modules, or by utilizing computer-readable data structures.

Of course, the methods and systems of the above-referenced embodiments may also include other additional elements, steps, computer-executable instructions, or computer-readable data structures.

The details of these and other embodiments of the present invention are set forth in the accompanying drawings and the description below. Other features and advantages of the invention will be apparent from the description and drawings, and from the claims.

BRIEF DESCRIPTION OF THE DRAWINGS

The present disclosure is illustrated by way of example and not limited in the accompanying figures in which like reference numerals indicate similar elements and in which:

FIGS. 1A-B illustrate an example of a system for providing personal training in accordance with example embodiments, wherein

DETAILED DESCRIPTION

In the following description of the various embodiments, reference is made to the accompanying drawings, which form a part hereof, and in which is shown by way of illustration various embodiments in which the disclosure may be practiced. It is to be understood that other embodiments may be utilized and structural and functional modifications may be made without departing from the scope and spirit of the present disclosure. Further, headings within this disclosure should not be considered as limiting aspects of the disclosure. Those skilled in the art with the benefit of this disclosure will appreciate that the example embodiments are not limited to the example headings.

I. Example Personal Training System

A. Illustrative Computing Devices

Figure 1A:
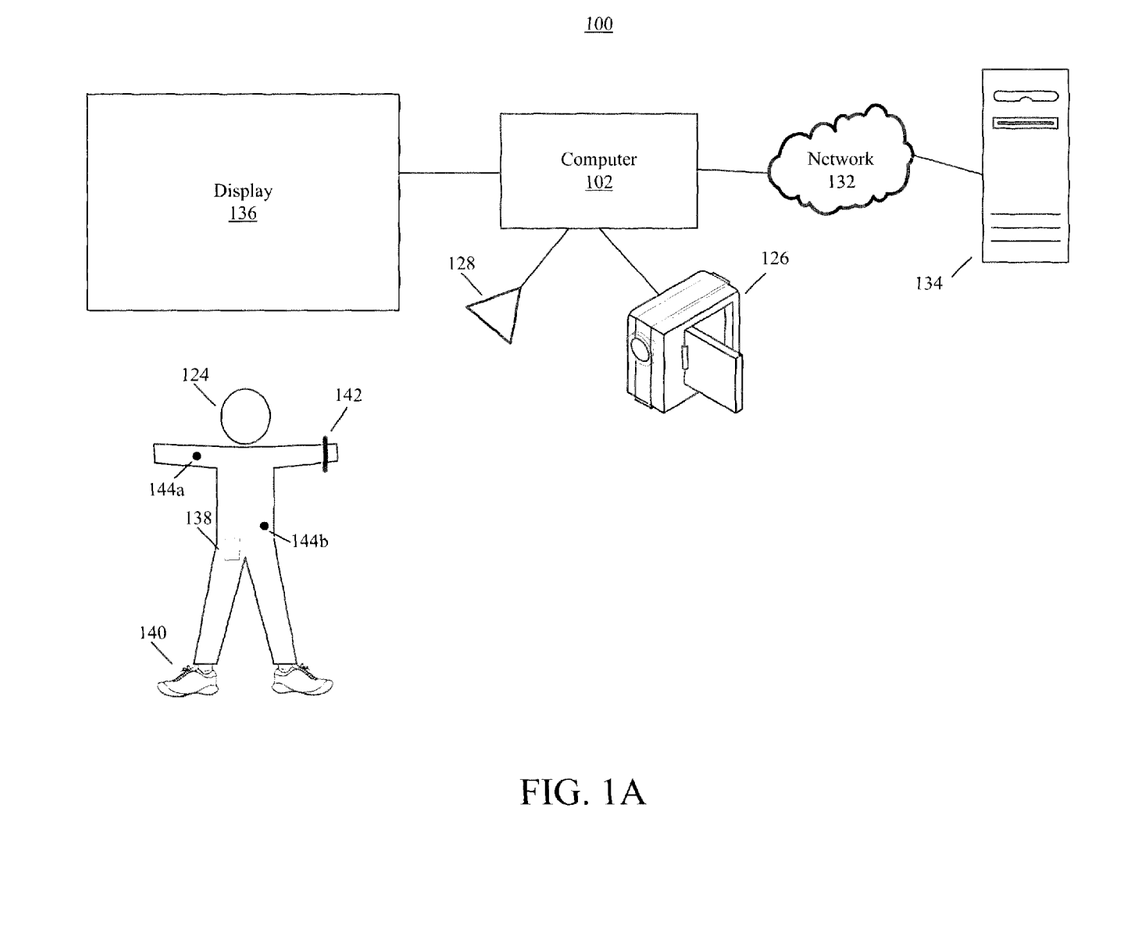
FIG. 1A illustrates an example network configured to monitor athletic activity.

FIG. 1A illustrates an example of a personal training system 100 in accordance with example embodiments. Example system 100 may include one or more electronic devices, such as computer 102. Computer 102 may comprise a mobile terminal, such as a telephone, music player, tablet, netbook or any portable device. In other embodiments, computer 102 may comprise a set-top box (STB), desktop computer, digital video recorder(s) (DVR), computer server(s), and/or any other desired computing device. In certain configurations, computer 102 may comprise a gaming console, such as for example, a Microsoft® XBOX, Sony® Playstation, and/or a Nintendo® Wii gaming consoles. Those skilled in the art will appreciate that these are merely example consoles for descriptive purposes and this disclosure is not limited to any console or device.

Figure 1B:
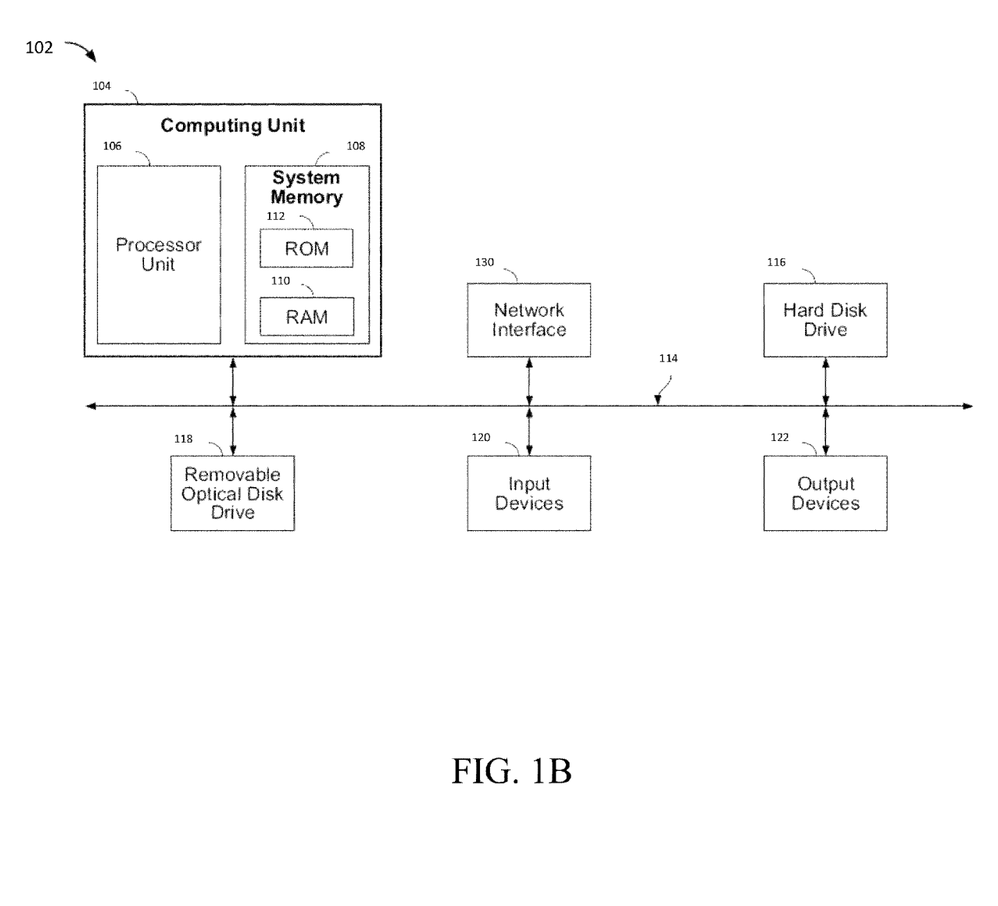
FIG. 1B illustrates an example computing device in accordance with example embodiments.

Turning briefly to FIG. 1B, computer 102 may include computing unit 104, which may comprise at least one processing unit 106. Processing unit 106 may be any type of processing device for executing software instructions, such as for example, a microprocessor device. Computer 102 may include a variety of non-transitory computer readable media, such as memory 108. Memory 108 may include, but is not limited to, random access memory (RAM) such as RAM 110, and/or read only memory (ROM), such as ROM 112. Memory 108 may include any of: electronically erasable programmable read only memory (EEPROM), flash memory or other memory technology, CD-ROM, digital versatile disks (DVD) or other optical disk storage, magnetic storage devices, or any other medium that can be used to store the desired information and that can be accessed by computer 102.

The processing unit 106 and the system memory 108 may be connected, either directly or indirectly, through a bus 114 or alternate communication structure to one or more peripheral devices. For example, the processing unit 106 or the system memory 108 may be directly or indirectly connected to additional memory storage, such as a hard disk drive 116, a removable magnetic disk drive, an optical disk drive 118, and a flash memory card. The processing unit 106 and the system memory 108 also may be directly or indirectly connected to one or more input devices 120 and one or more output devices 122. The output devices 122 may include, for example, a display device 136, television, printer, stereo, or speakers. In some embodiments one or more display devices may be incorporated into eyewear. The display devices incorporated into eyewear may provide feedback to users. Eyewear incorporating one or more display devices also provides for a portable display system. The input devices 120 may include, for example, a keyboard, touch screen, a remote control pad, a pointing device (such as a mouse, touchpad, stylus, trackball, or joystick), a scanner, a camera or a microphone. In this regard, input devices 120 may comprise one or more sensors configured to sense, detect, and/or measure athletic movement from a user, such as user 124, shown in FIG. 1A.

Looking again to FIG. 1A, image-capturing device 126 and/or sensor 128 may be utilized in detecting and/or measuring athletic movements of user 124. In one embodiment, data obtained from image-capturing device 126 or sensor 128 may directly detect athletic movements, such that the data obtained from image-capturing device 126 or sensor 128 is directly correlated to a motion parameter. Yet, in other embodiments, data from image-capturing device 126 and/or sensor 128 may be utilized in combination, either with each other or with other sensors to detect and/or measure movements. Thus, certain measurements may be determined from combining data obtained from two or more devices. Image-capturing device 126 and/or sensor 128 may include or be operatively connected to one or more sensors, including but not limited to: an accelerometer, a gyroscope, a location-determining device (e.g., GPS), light sensor, temperature sensor (including ambient temperature and/or body temperature), heart rate monitor, image-capturing sensor, moisture sensor and/or combinations thereof. Example uses of illustrative sensors 126, 128 are provided below in Section I.C, entitled "Illustrative Sensors." Computer 102 may also use touch screens or image capturing device to determine where a user is pointing to make selections from a graphical user interface. One or more embodiments may utilize one or more wired and/or wireless technologies, alone or in combination, wherein examples of wireless technologies include Bluetooth® technologies, Bluetooth® low energy technologies, and/or ANT technologies.

B. Illustrative Network

Computer 102, computing unit 104, and/or any other electronic devices may be directly or indirectly connected to one or more network interfaces, such as example interface 130 (shown in FIG. 1B) for communicating with a network, such as network 132. In the example of FIG. 1B, network interface 130, may comprise a network adapter or network interface card (NIC) configured to translate data and control signals from the computing unit 104 into network messages according to one or more communication protocols, such as the Transmission Control Protocol (TCP), the Internet Protocol (IP), and the User Datagram Protocol (UDP). These protocols are well known in the art, and thus will not be discussed here in more detail. An interface 130 may employ any suitable connection agent for connecting to a network, including, for example, a wireless transceiver, a power line adapter, a modem, or an Ethernet connection. Network 132, however, may be any one or more information distribution network(s), of any type(s) or topology(s), alone or in combination(s), such as internet(s), intranet(s), cloud(s), LAN(s). Network 132 may be any one or more of cable, fiber, satellite, telephone, cellular, wireless, etc. Networks are well known in the art, and thus will not be discussed here in more detail. Network 132 may be variously configured such as having one or more wired or wireless communication channels to connect one or more locations (e.g., schools, businesses, homes, consumer dwellings, network resources, etc.), to one or more remote servers 134, or to other computers, such as similar or identical to computer 102. Indeed, system 100 may include more than one instance of each component (e.g., more than one computer 102, more than one display 136, etc.).

Regardless of whether computer 102 or other electronic device within network 132 is portable or at a fixed location, it should be appreciated that, in addition to the input, output and storage peripheral devices specifically listed above, the computing device may be connected, such as either directly, or through network 132 to a variety of other peripheral devices, including some that may perform input, output and storage functions, or some combination thereof. In certain embodiments, a single device may integrate one or more components shown in FIG. 1A. For example, a single device may include computer 102, image-capturing device 126, sensor 128, display 136 and/or additional components. In one embodiment, sensor device 138 may comprise a mobile terminal having a display 136, image-capturing device 126, and one or more sensors 128. Yet, in another embodiment, image-capturing device 126, and/or sensor 128 may be peripherals configured to be operatively connected to a media device, including for example, a gaming or media system. Thus, it goes from the foregoing that this disclosure is not limited to stationary systems and methods. Rather, certain embodiments may be carried out by a user 124 in almost any location.

C. Illustrative Sensors

Computer 102 and/or other devices may comprise one or more sensors 126, 128 configured to detect and/or monitor at least one fitness parameter of a user 124. Sensors 126 and/or 128 may include, but are not limited to: an accelerometer, a gyroscope, a location-determining device (e.g., GPS), light sensor, temperature sensor (including ambient temperature and/or body temperature), sleep pattern sensors, heart rate monitor, image-capturing sensor, moisture sensor and/or combinations thereof. Network 132 and/or computer 102 may be in communication with one or more electronic devices of system 100, including for example, display 136, an image capturing device 126 (e.g., one or more video cameras), and sensor 128, which may be an infrared (IR) device. In one embodiment sensor 128 may comprise an IR transceiver. For example, sensors 126, and/or 128 may transmit waveforms into the environment, including towards the direction of user 124 and receive a "reflection" or otherwise detect alterations of those released waveforms. In yet another embodiment, image-capturing device 126 and/or sensor 128 may be configured to transmit and/or receive other wireless signals, such as radar, sonar, and/or audible information. Those skilled in the art will readily appreciate that signals corresponding to a multitude of different data spectrums may be utilized in accordance with various embodiments. In this regard, sensors 126 and/or 128 may detect waveforms emitted from external sources (e.g., not system 100). For example, sensors 126 and/or 128 may detect heat being emitted from user 124 and/or the surrounding environment. Thus, image-capturing device 126 and/or sensor 128 may comprise one or more thermal imaging devices. In one embodiment, image-capturing device 126 and/or sensor 128 may comprise an IR device configured to perform range phenomenology. As a non-limited example, image-capturing devices configured to perform range phenomenology are commercially available from Flir Systems, Inc. of Portland, Oreg. Although image capturing device 126 and sensor 128 and display 136 are shown in direct (wirelessly or wired) communication with computer 102, those skilled in the art will appreciate that any may directly communicate (wirelessly or wired) with network 132.

1. Multi-Purpose Electronic Devices

User 124 may possess, carry, and/or wear any number of electronic devices, including sensory devices 138, 140, 142, and/or 144. In certain embodiments, one or more devices 138, 140, 142, 144 may not be specially manufactured for fitness or athletic purposes. Indeed, aspects of this disclosure relate to utilizing data from a plurality of devices, some of which are not fitness devices, to collect, detect, and/or measure athletic data. In one embodiment, device 138 may comprise a portable electronic device, such as a telephone or digital music player, including an IPOD®, IPAD®, or iPhone®, brand devices available from Apple, Inc. of Cupertino, Calif. or Zune® or Microsoft® Windows devices available from Microsoft of Redmond, Wash. As known in the art, digital media players can serve as both an output device for a computer (e.g., outputting music from a sound file or pictures from an image file) and a storage device. In one embodiment, device 138 may be computer 102, yet in other embodiments, computer 102 may be entirely distinct from device 138. Regardless of whether device 138 is configured to provide certain output, it may serve as an input device for receiving sensory information. Devices 138, 140, 142, and/or 144 may include one or more sensors, including but not limited to: an accelerometer, a gyroscope, a location-determining device (e.g., GPS), light sensor, temperature sensor (including ambient temperature and/or body temperature), heart rate monitor, image-capturing sensor, moisture sensor and/or combinations thereof. In certain embodiments, sensors may be passive, such as reflective materials that may be detected by image-capturing device 126 and/or sensor 128 (among others). In certain embodiments, sensors 144 may be integrated into apparel, such as athletic clothing. For instance, the user 124 may wear one or more on-body sensors 144*a-b*. Sensors 144 may be incorporated into the clothing of user 124 and/or placed at any desired location of the body of user 124. Sensors 144 may communicate (e.g., wirelessly) with computer 102, sensors 128, 138, 140, and 142, and/or camera 126. Examples of interactive gaming apparel are described in U.S. patent application Ser. No. 10/286,396, filed Oct. 30, 2002, and published as U.S. Pat. Pub. No. 2004/0087366, the contents of which are incorporated herein by reference in its entirety for any and all non-limiting purposes. In certain embodiments, passive sensing surfaces may reflect waveforms, such as infrared light, emitted by image-capturing device 126 and/or sensor 128. In one embodiment, passive sensors located on user's 124 apparel may comprise generally spherical structures made of glass or other transparent or translucent surfaces which may reflect waveforms. Different classes of apparel may be utilized in which a given class of apparel has specific sensors configured to be located proximate to a specific portion of the user's 124 body when properly worn. For example, golf apparel may include one or more sensors positioned on the apparel in a first configuration and yet soccer apparel may include one or more sensors positioned on apparel in a second configuration.

Devices 138-144 may communicate with each other, either directly or through a network, such as network 132. Communication between one or more of devices 138-144 may take place via computer 102. For example, two or more of devices 138-144 may be peripherals operatively connected to bus 114 of computer 102. In yet another embodiment, a first device, such as device 138 may communicate with a first computer, such as computer 102 as well as another device, such as device 142, however, device 142 may not be configured to connect to computer 102 but may communicate with device 138. Those skilled in the art will appreciate that other configurations are possible.

Some implementations of the example embodiments may alternately or additionally employ computing devices that are intended to be capable of a wide variety of functions, such as a desktop or laptop personal computer. These computing devices may have any combination of peripheral devices or additional components as desired. Also, the components shown in FIG. 1B may be included in the server 134, other computers, apparatuses, etc.

2. Illustrative Apparel/Accessory Sensors

In certain embodiments, sensory devices 138, 140, 142 and/or 144 may be formed within or otherwise associated with user's 124 clothing or accessories, including a watch, armband, wristband, necklace, shirt, shoe, or the like. Examples of shoe-mounted and wrist-worn devices (devices 140 and 142, respectively) are described immediately below, however, these are merely example embodiments and this disclosure should not be limited to such.

i. Shoe-Mounted Device

Figure 2A:
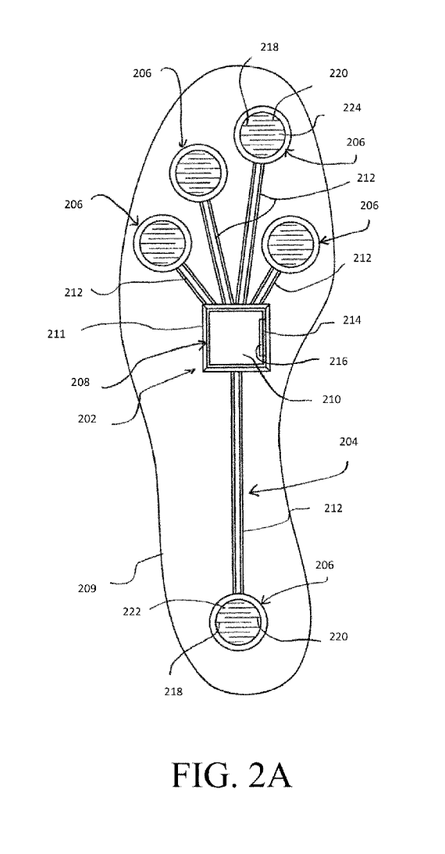
FIGS. 2A-B illustrate example sensor assemblies that may be worn by a user in accordance with example embodiments.

In certain embodiments, sensory device 140 may comprise footwear which may include one or more sensors, including but not limited to: an accelerometer, location-sensing components, such as GPS, and/or a force sensor system. FIG. 2A illustrates one example embodiment of a sensor system 202. In certain embodiments, system 202 may include a sensor assembly 204. Assembly 204 may comprise one or more sensors, such as for example, an accelerometer, location-determining components, and/or force sensors. In the illustrated embodiment, assembly 204 incorporates a plurality of sensors, which may include force-sensitive resistor (FSR) sensors 206. In yet other embodiments, other sensor(s) may be utilized. Port 208 may be positioned within a sole structure 209 of a shoe. Port 208 may optionally be provided to be in communication with an electronic module 210 (which may be in a housing 211) and a plurality of leads 212 connecting the FSR sensors 206 to the port 208. Module 210 may be contained within a well or cavity in a sole structure of a shoe. The port 208 and the module 210 include complementary interfaces 214, 216 for connection and communication.

In certain embodiments, at least one force-sensitive resistor 206 shown in FIG. 2A may contain first and second electrodes or electrical contacts 218, 220 and a force-sensitive resistive material 222 disposed between the electrodes 218, 220 to electrically connect the electrodes 218, 220 together. When pressure is applied to the force-sensitive material 222, the resistivity and/or conductivity of the force-sensitive material 222 changes, which changes the electrical potential between the electrodes 218, 220. The change in resistance can be detected by the sensor system 202 to detect the force applied on the sensor 216. The force-sensitive resistive material 222 may change its resistance under pressure in a variety of ways. For example, the force-sensitive material 222 may have an internal resistance that decreases when the material is compressed, similar to the quantum tunneling composites described in greater detail below. Further compression of this material may further decrease the resistance, allowing quantitative measurements, as well as binary (on/off) measurements. In some circumstances, this type of force-sensitive resistive behavior may be described as "volume-based resistance," and materials exhibiting this behavior may be referred to as "smart materials." As another example, the material 222 may change the resistance by changing the degree of surface-to-surface contact. This can be achieved in several ways, such as by using microprojections on the surface that raise the surface resistance in an uncompressed condition, where the surface resistance decreases when the microprojections are compressed, or by using a flexible electrode that can be deformed to create increased surface-to-surface contact with another electrode. This surface resistance may be the resistance between the material 222 and the electrode 218, 220 222 and/or the surface resistance between a conducting layer (e.g., carbon/graphite) and a force-sensitive layer (e.g., a semiconductor) of a multi-layer material 222. The greater the compression, the greater the surface-to-surface contact, resulting in lower resistance and enabling quantitative measurement. In some circumstances, this type of force-sensitive resistive behavior may be described as "contact-based resistance." It is understood that the force-sensitive resistive material 222, as defined herein, may be or include a doped or non-doped semiconducting material.

The electrodes 218, 220 of the FSR sensor 216 can be formed of any conductive material, including metals, carbon/graphite fibers or composites, other conductive composites, conductive polymers or polymers containing a conductive material, conductive ceramics, doped semiconductors, or any other conductive material. The leads 212 can be connected to the electrodes 218, 220 by any suitable method, including welding, soldering, brazing, adhesively joining, fasteners, or any other integral or non-integral joining method. Alternately, the electrode 218, 220 and associated lead 212 may be formed of a single piece of the same material.

ii. Wrist-Worn Device

Figure 2B:
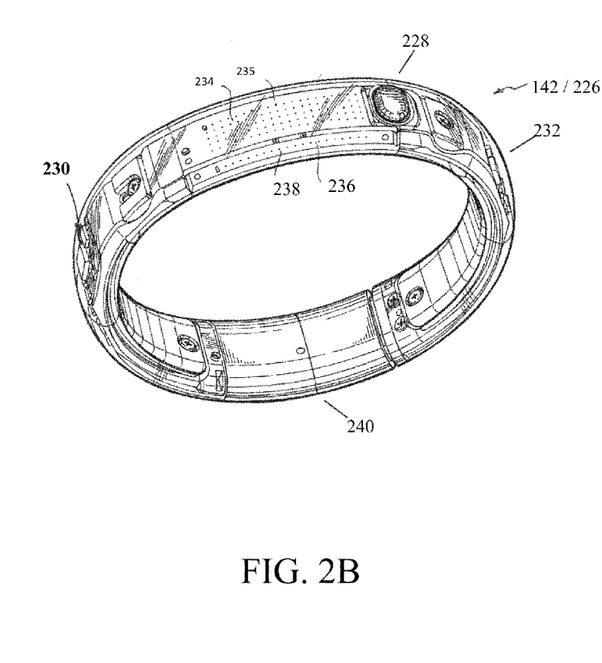

As shown in FIG. 2B, device 226 (which may resemble or be sensory device 142 shown in FIG. 1A) may be configured to be worn by user 124, such as around a wrist, arm, ankle or the like. Device 226 may monitor athletic movements of a user, including all-day activity of user 124. In this regard, device assembly 226 may detect athletic movement during user's 124 interactions with computer 102 and/or operate independently of computer 102. For example, in one embodiment, device 226 may be an-all day activity monitor that measures activity regardless of the user's proximity or interactions with computer 102. Device 226 may communicate directly with network 132 and/or other devices, such as devices 138 and/or 140. In other embodiments, athletic data obtained from device 226 may be utilized in determinations conducted by computer 102, such as determinations relating to which exercise programs are presented to user 124. In one embodiment, device 226 may also wirelessly interact with a mobile device, such as device 138 associated with user 124 or a remote website such as a site dedicated to fitness or health related subject matter. At some predetermined time, the user may wish to transfer data from the device 226 to another location.

As shown in FIG. 2B, device 226 may include an input mechanism, such as a depressible input button 228 assist in operation of the device 226. The input button 228 may be operably connected to a controller 230 and/or any other electronic components, such as one or more of the elements discussed in relation to computer 102 shown in FIG. 1B. Controller 230 may be embedded or otherwise part of housing 232. Housing 232 may be formed of one or more materials, including elastomeric components and comprise one or more displays, such as display 234. The display may be considered an illuminable portion of the device 226. The display 234 may include a series of individual lighting elements or light members such as LED lights 234 in an exemplary embodiment. The LED lights may be formed in an array and operably connected to the controller 230. Device 226 may include an indicator system 236, which may also be considered a portion or component of the overall display 234.

It is understood that the indicator system 236 can operate and illuminate in conjunction with the display 234 (which may have pixel member 235) or completely separate from the display 234. The indicator system 236 may also include a plurality of additional lighting elements or light members 238, which may also take the form of LED lights in an exemplary embodiment. In certain embodiments, indicator system may provide a visual indication of goals, such as by illuminating a portion of lighting members 238 to represent accomplishment towards one or more goals.

A fastening mechanism 240 can be unlatched wherein the device 226 can be positioned around a wrist of the user 124 and the fastening mechanism 240 can be subsequently placed in a latched position. The user can wear the device 226 at all times if desired. In one embodiment, fastening mechanism 240 may comprise an interface, including but not limited to a USB port, for operative interaction with computer 102 and/or devices 138, 140.

In certain embodiments, device 226 may comprise a sensor assembly (not shown in FIG. 2B). The sensor assembly may comprise a plurality of different sensors. In an example embodiment, the sensor assembly may comprise or permit operative connection to an accelerometer (including in the form of a multi-axis accelerometer), heart rate sensor, location-determining sensor, such as a GPS sensor, and/or other sensors. Detected movements or parameters from device's 142 sensor(s), may include (or be used to form) a variety of different parameters, metrics or physiological characteristics including but not limited to speed, distance, steps taken, and energy expenditure such as calories, heart rate, sweat detection, effort, oxygen consumed, and/or oxygen kinetics. Such parameters may also be expressed in terms of activity points or currency earned by the user based on the activity of the user.

II. Energy Expenditure Point Calculations

Figure 3:
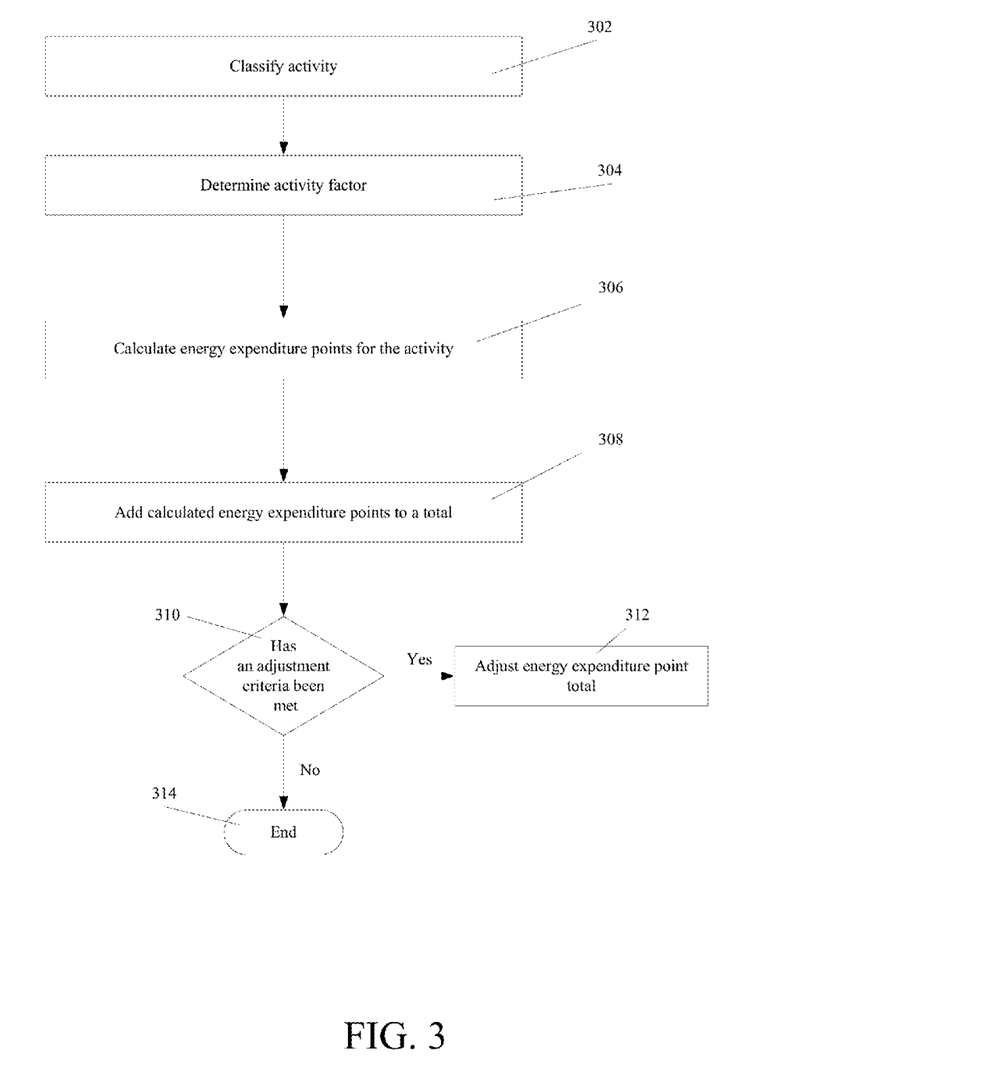
FIG. 3 illustrates a method for calculating energy expenditure, in accordance with an embodiment of the invention.

FIG. 3 illustrates a method for calculating energy expenditure values, such as points, in accordance with an embodiment of the invention. Certain embodiments may classify physical motions of a user. For example, at illustrative step 302, one or more activities may be classified. System 100 may process data received from one or more of the sensors described above to attempt to classify a user's activity. For example, system 100 may compare a sensor signal to one or more signal or activity "templates" or "signatures" corresponding to selected activities. In certain embodiments, templates may be created by attaching sensors to a user and monitoring signals generated when the user performs various activities. In accordance with certain embodiments, an activity may be associated with an activity template specific to user 124. In one such embodiment, user 124 may be assigned a default template for a specific activity unless a specific template has been assigned to that activity. Thus, user 124 may create or receive (but is not required to create or receive) an activity template that may be more accurate than a default template because the template is more specific to the user and/or the activity. User 124 may have the option to create templates for one or more predefined or undefined activities. A specific or otherwise new template might be shared among the community of users. Shared templates may be based on a variety of different sensors. In some embodiments templates may be refined or adjusted for use with different sensors. For example, a template that was created for use with a shoe based sensor may be refined for use with a wrist worn sensor.

An activity template may be created from data obtained from one or more of a plurality of different sensors. For example, a first group of sensors (e.g. sensors 126 and 138)

may be utilized in the formation or refinement of a first activity template; however, a second group of sensors (e.g., sensors 128 and 140) may be utilized in the formation or refinement of a second activity template. In yet further embodiments, a third group of sensors, such as sensors 128 and 140 (and/or other sensors), may be utilized in the creation of the first activity template for a second user (e.g., not user 124) than utilized for the formation of the same activity template as user 124. Thus, in accordance with certain embodiments, there is no requirement that data from a specific sensor be received for either: 1) the same activity template for different users; and/or 2) different activity templates for the same user.

In one embodiment, a wrist mounted accelerometer, which may be a multi-axis accelerometer, may be attached to a user and signal templates based on the accelerometer output when the user runs, walks, etc. may be created. The templates may be functions of the sensor(s) used and/or the locations of the sensor(s). In some embodiments, a single signal (or value) is created by combining multiple signals (or values). For example, three outputs of a three axis accelerometer may be summed or otherwise combined to create one or more signals. Example step 302 may include comparing a signal, multiple signals or a combination of signals to one or more templates. In some embodiments, a best match approach may be implemented in which every activity is attempted to be classified. In other embodiments, if a signal, multiple signals or combination of signals does not sufficiently match a template, the activity may remain unclassified.

After at least one of user's 124 activities is classified, step 304 may be implemented to determine a corresponding activity factor. An activity factor may correspond to brisk running, running at a moderate pace, walking slowly or any other activity. An activity factor for an activity may be related to calories or energy generally required to perform the activity. If an activity was not classified in step 302, a default activity factor may be selected or derived. In some embodiments multiple default activity factors may be utilized. An activity's intensity, duration or other characteristic(s) may be assessed, from which one or more default activity factors may be applied. The plural activity factors may be set via medians/averages, ranges, or other statistical approaches.

In various embodiments of the invention, activity factors are used to calculate energy expenditure points. After at least one of user's 124 activities is classified, in step 306 energy expenditure points may be calculated. The use of energy expenditure points allows for comparison of activity levels and may promote collaboration among users, normalize for competition among users of different capabilities, and otherwise encourage activity. In one embodiment, energy expenditure points are calculated as follows:

$$EEPs = AF * duration \quad \text{(equation 1)}$$

Wherein:
EEPs=energy expenditure points
AF=activity factor determined in step 304
duration=duration of the activity classified in step 302

Step 306 may be performed at a device that includes sensors that monitor activity and/or at another device that includes a processor, such as a mobile phone (see, e.g., 138) or server (see, e.g., 134).

In some embodiments equation 1 may be modified to include a scalar that is multiplied by the activity factor and duration. The scalar may be selected so that typical energy expenditure points fall within a desired range. The range of points may be desired for various games or competitions.

Variations of equation 1 may be used in other embodiments of the invention. In some embodiments, users may select an equation and/or one or more variables, such as for example, a scalar. Equations may be selected for different games and competitions. In one example a group may set handicaps among the players based on fitness, so that the most fit generate EEPs only if they do a common activity or set of activities for longer period(s) of time. A group of users participating in an energy expenditure point competition may agree on a particular equation or method before beginning the competition. In some embodiments of the invention, a user may participate in multiple competitions and earn different points for the same activity because of different calculation methods. For example, a user may be participating in two competitions that have unique calculation methods. The user may earn two different point totals for the two different games and a third point total foe their overall energy expenditure. Some point totals may be maintained separate from an overall point total.

Alternative embodiments of the invention may use alternative or additional equations for calculating point values and/or other quantities. The equations may include derivations of measured and/or calculated values. Derivations that include time periods may be used to show rates and rates of change. For example, one equation may be used to determine a rate of accumulating activity points or energy expenditure points. Another equation may be used to determine a quantity of activity points or energy expenditure points accumulated over a predetermined time period.

Some equations may use variables other than time. For example, some equations may be used to calculate a value as a function of activity points or energy expenditure points and steps. Calculating values that are functions of activity points or energy expenditure points and other variables may be used to compare the efficiencies of various activities. For example, an equation may be used to determine that taking steps at a faster pace may result in activity points or energy expenditure points accumulating at a faster per step pace. Another exemplary equation may determine activity points or energy expenditure points per a predetermined distance or a unit of distance.

Some equations may be used to calculate first and/or second derivatives of measured or calculated values to show rates and rates of change. For example, an equation may be used to calculate or estimate a rate of accumulation of activity points or energy expenditure points at a given time. In some embodiments an instantaneous rate of accumulation of activity points or energy expenditure points is displayed to a user via display 235 or a display that is part of a mobile device.

After the energy expenditure points are calculated, the calculated points may be combined, such as being added, to a total in step 308. The total may allow user 124 (and/or selected individuals or groups approved by user 124) to see how many points are earned over various periods of time, such as days, weeks and months. Totals may also be calculated for multiple time periods. For example, a user may receive totals for periods that include 24 hours, one week, one month and one year. In some embodiments users may select other time periods or deselect time periods. A user may track multiple time periods concurrently and track points award since the beginning of use of a device or start of a program. The total for any giving time period may represent points earned for several activities. For example, in a day a user may receive points for walking, jogging and sprinting during different time periods. As mentioned above, the points earned for each activity may be a function of a corresponding activity factor.

Energy expenditure points may be deducted when user 124 has been inactive for a predetermined period of time or enhanced when certain criteria are met. This feature may be included with all calculations or may be used in various games and competitions. For example, in step 314 it may be determined whether an adjustment criteria has been met. The adjustment criteria may include inactivity for a predetermined time period. In some embodiments inactivity is not determined by merely determining that an amount of time has passed since with user was active.

When an adjustment criteria has been met, the total of energy expenditure points may be adjusted in step 310. The adjustment may be a function of duration of inactivity. In some embodiments, a device may warn user 124 (or authorized groups/individuals) that they are close to receiving a reduction in energy expenditure points to encourage activity. It yet other embodiments, an alarm may notify user 124 (and/or other authorized individuals and/or groups) that they have received a reduction of energy expenditure points. In certain embodiments, team-mates and/or competing users may be notified of a reduction (or potential for reduction). In further embodiments, teachers, trainers, and/or parents may more readily monitor the physical activity of others. When a user has not been inactive, the process may end in step 314. Of course, the method shown in FIG. 3 may be repeated at various intervals and allow for tracking points concurrently for different time periods, such as days, weeks and years.

In another aspect, a device 10, such as device 226 may provide a message based on inactivity or non-active periods. If the device senses that the user has been in a non-active (e.g., low activity) state for a predetermined amount of time, an alert message may be delivered to the indicator system or display to remind the user to become more active. The alert message can be delivered in any of the manners described herein. The threshold levels of a low activity state and amount of inactive time could also vary and be individually set by the user.

In some arrangements, user non-activity or inactivity may also be detected and affect the user's progress toward completion of an activity goal. For example, inactivity may be detected when a user does not exhibit movement of a particular level or a type of movement for a specified amount of time, does not exhibit a heart rate of at least a threshold level, does not move a sufficient amount of distance over an amount of time and the like and/or combinations thereof. For arrangements in which a user accumulates activity points to reach an activity point goal, points or a value may be deducted from the user's activity point or other activity metric total when an amount of non-activity (e.g., inactivity or sedentary state) is detected. Various conversion rates for converting inactivity to activity point deductions may be used. In a particular example, 10 minutes of inactivity may correspond to a 5 point deduction. In another example, 30 minutes of inactivity may correspond to a 100 point deduction. Loss or deduction of activity points may be linear or may be non-linear, for example, exponential, parabolic and the like.

A user's non-active time may include inactive time and sedentary time. Inactivity and sedentary time may be defined by different movement, heart-rate, step or other thresholds or may be defined using the same thresholds. In one example, sedentary time may have a higher threshold (e.g., requiring a higher level of activity) than an inactivity threshold. That is, an individual may be considered sedentary but not inactive. The non-active threshold may correspond to the sedentary threshold or a higher threshold, if desired. Alternatively, an inactivity threshold may be greater than a sedentary threshold. There may also be multiple sedentary thresholds, inactivity thresholds and/or non-active thresholds (e.g., each of the sedentary and inactivity thresholds may be a non-active threshold). Different point deductions or rates of point deductions may also be defined between the multiple thresholds and levels of little to no activity (e.g., non-activity). For example, a user may lose 50 points per hour for inactivity and 30 points per hour for sedentary activity or vice versa. Further, activity point deduction may be triggered at different times depending on if the user is inactive or sedentary. For instance, a user may begin losing activity points after 30 minutes of inactivity or 45 minutes of being sedentary. Additional thresholds (e.g., more than two thresholds) and corresponding rates of activity point loss may also be defined.

In some arrangements, various sensors may be used to detect non-active periods of time. As discussed, non-activity time periods may be defined based on heart-rate, amplitude of a movement signal, step rate (e.g., <10 steps per minute), or the like. Alternatively or additionally, inactivity and sedentary time periods may be measured based on a physical position, body position, body orientation, body posture of or type of activity being performed by the individual. The detrimental effects of various physical inactivity or sedentary body positions or orientations may also differ. Accordingly, 30 minutes of reclining may introduce the same health risks as 45 minutes of sitting. The potential for health risks may also be time-dependent. Accordingly, non-activity (e.g., sleeping) for a specified range of durations and during a specified range of time might not introduce health risks. In one example, sleeping for 7-9 hours between 9 PM and 9 AM might not introduce detrimental health risks and thus, might not contribute to activity point or other activity metric value deduction. Indeed, in some example, a lack of inactivity (such as sleep) for a specified range of durations and/or during a specified range of time may be considered detrimental to a user's health. Thus, activity points may be deducted or activity points may be accumulated at a slower rate during these times.

Alternatively or additionally, the amount by which a value of the activity metric (e.g., an activity points) is decreased may be determined based on time of day, location of the user, physical position of the user, level of inactivity and the like. For example, a user may lose greater value in an activity metric and/or at a faster rate during the afternoon than during the evenings. In another example, if a user is at a gym, the user may lose fewer activity points or other activity metric or lose value in the metric at a slower rate than if the user was located at home.

To account for the variances in types of non-active activity (e.g., below a requisite level of movement to be considered activity), a system may distinguish between physical body positions or orientations including, for example, sleeping, reclining, sitting and standing. Distinguishing between different physical body positions and orientations may include placing sensors at different locations of the user's body to detect the individual positions of each body part. The physical body position of the user may then be determined based on the relative positions of the body parts to one another. For example, when a knee location sensor is within a first threshold distance of a waist or chest sensor, the system may determine that the user is sitting. If the knee location sensor is outside of the first threshold distance, the system may determine that the user is standing. In the above example, the system may use a portion of the distance such as the vertical distance. By using vertical distance alone or in combination with an absolute distance (e.g., straight line distance between the two sensors), the system may further distinguish between when a user is lying down and standing up. For example, a lying down position may correspond to a very low vertical distance between the knee sensor and chest or waist sensor even though the absolute distance may be larger. A standing position may correspond to a larger vertical distance between the knee sensor and the waist or chest sensor but exhibit a similar absolute distance. In other examples, an angle formed by the various sensors may be used to determine an individual's position. Additionally or alternatively, the location of the user's various body parts may be evaluated in conjunction with accelerometer or movement data to determine if the user is exhibiting movement or (e.g., at, above or below) a specified level of movement.

In addition to deductions in activity points, the system may alert a user to inactivity to encourage active lifestyles. In one example, the system may alert the user by displaying a message or indicator on a device such as the wearable device assembly described herein after a specified amount of inactivity such as 2 minutes, 5 minutes, 30 minutes, 1 hour and the like. The amount of inactivity time may be additive over non-consecutive time periods. An amount of consecutive inactivity time may alternatively or additionally be tracked. For example, if the user is inactive between 10:15 and 11:00 AM and then again between 2:00 and 2:30 PM, the total amount of non-active time may be 1 hour and 15 minutes. The message or indicator of inactivity may be provided as a warning prior to deducting activity points. For example, the message may indicate that X amount of activity points will be deducted if the user does not exhibit a sufficient level of activity within a specified amount of time (e.g., 30 minutes, 5 minutes, 10 seconds, 30 seconds, 1 hour, 2 hours, etc.). Accordingly, the device may include a non-active timer to determine the amount of user non-activity. Additionally, the message may provide a suggestion as to a type of activity the user should perform to counter any risks introduced by the inactivity. For example, the system may suggest that the user walk 1 hour at a 10 minute mile pace. When the user has counteracted or accounted for the risks or negative effects of the detected amount of inactivity time, a celebratory message or other indication may be provided.

Warnings, point deductions and/or other notifications may be provided if a user returns to a sedentary or a non-active mode within a specified amount of time of exiting sedentary or a non-active mode. For example, the user may exercise or exhibit a sufficient level of activity to exit the sedentary or a non-active mode for a period of 10 minutes. However, the system or device may require at least 30 minutes of activity to avoid additional warnings for a period of time such as 1 hour, 2 hours, 3 hours, etc. For example, the warnings may indicate that the user did not exhibit activity for a sufficient amount of time or a sufficient level of activity or a combination thereof. Additionally, multiple sedentary periods within short amounts of time (e.g., a threshold amount of time) may require higher or additional levels of activity to counteract potential sedentary effects including health risks and the like. In a particular example, the user may be required to perform a higher level of activity to halt point deduction.

The device or other system may further advise a user as to an amount of non-active time allowed before negative health effects may occur. In one example, the device or system may include a countdown indicating a remaining amount of allowable non-active time before potential health risks may begin taking effect. An amount of permissible non-active time may be earned or accumulated based on an amount of activity performed. Accordingly, the device may also provide suggestions or recommendations as to a type and/or duration of activity that may be performed to earn a specified amount of non-active time (e.g., 1 hour of TV watching). Different types of non-active or sedentary activities may require different types or amounts of activity. For example, 1 hour of reclining may require more strenuous or longer exercise than 1 hour of sitting. In another example, 1 hour of sitting while knitting may require less strenuous or a lower amount of exercise or activity than 1 hour of sitting while watching television. According to one or more arrangements, recommendations may be generated based on empirical data and/or predefined programming and data tables specifying a type and/or duration of activity and a corresponding amount of permissible non-activity.

The device or activity tracking system may further recommend activities based on historical records. For instance, the device or tracking system may determine activity performed by the user in the past and generate recommendations based on those types of activities. Additionally or alternatively, the device or tracking system may generate recommendations for specific workouts performed by the user in the past. For example, a user may need to perform 500 calories worth of activity to counteract 2 hours of TV watching. In such a case, the system may recommend a particular workout performed by the user in the past in which the user burned 500 calories. Combinations of historical activity types and specific historical workouts may be used to generate recommendations. In one example, the system may recommend one of two workouts that the user has performed in the past based on a type of workout that the user appears to prefer. The preference may be determined based on a number of times the user has performed each type of workout. A workout or activity type may also be recommended based on location and time. For example, if a user previously performs a particular type of activity or a particular workout routine at the same location and/or at the same time, the system may recommend that type of activity or workout routine. Other recommendations algorithms and factors may be used.

System 100 may be configured to transmit energy expenditure points to a social networking website. The users may be ranked based on their total number of points for a desired time interval (e.g., rank by day, week, month, year, etc.).

Figure 4:
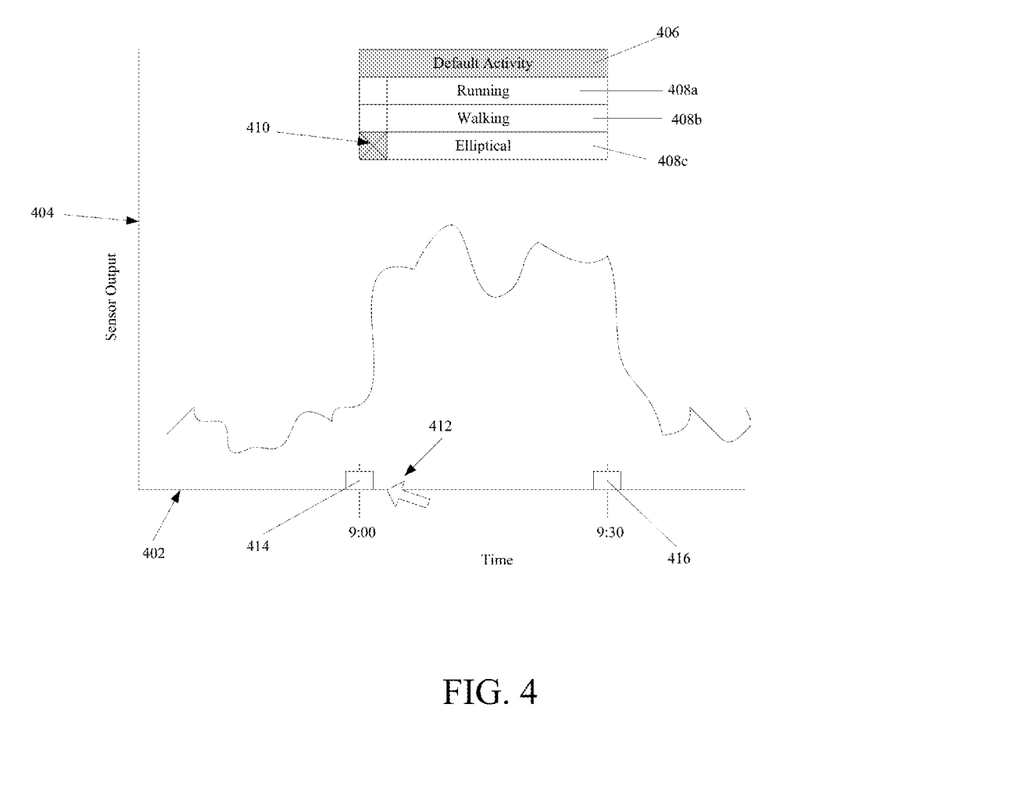
FIG. 4 illustrates a graphical user interface that may be used to adjust activity factors in accordance with an embodiment of the invention.

FIG. 4 illustrates a graphical user interface that may be used to adjust activity factors in accordance with an embodiment of the invention. Time is represented along an axis 402 and the magnitude of a sensor output or combination of outputs from sensors is represented along an axis 404. The interface shows that a user performed some activity between 9:00 and 9:30. Element 406 shows that the activity has been given a default classification. Drop down elements 408*a*, 408*b* and 408*c* provide options for selecting running, walking and elliptical respectively. The options provided in elements 408*a*, 408*b* and 408*c* may be the closest activities that were identified in step 302 above. Users may use a graphical user interface element, such as check box 410 to select an appropriate activity. A cursor 412 may be used to select a time period.

A time period may be selected by moving sliding block elements 414 and 416 that are configured to move along axis 402. The input provided by the user may be considered an estimate in some embodiments and a user worn device, computer device or some other device may determine an actual start and/or stop time. For example, a user may identify that he or she started an activity at 9:00 and a device may analyze sensor data, data derived from sensor data and or various other analytic data to determine that the user actually started at 9:02. Activity and energy expenditure point calculations may be determined with the determined start time. Sliding block elements 414 and 416 may also include widths set by users to establish confidence ranges. For example, a user may set sliding block element 414 to span a 10 minute interval over which the user believes that he or she started an activity. An algorithm may try to determine a start time in that interval.

Ending times may be determined in a similar manner. Alternative embodiments may use the beginning, middle or end of the start time span identified with sliding block element 414 and the beginning, middle or end of the stop time span identified with sliding block element 416. Still other alternative embodiments may determine the most likely start and stop times by analyzing sensor data, data derived from sensor data and or various other analytic data along with the beginning, middle and end of the time periods identified with each of sliding block elements 414 and 416 to determine start and stop times.

The graphical user interface shown in FIG. 4 allows users to more accurately classify known activities. In some embodiments the options available to users are limited to likely activities. Limiting the options available can increase the integrity of games and competitions. In other embodiments users can select any activity supported by the system. In still other embodiments user can create new activities that will then correspond to the indicated sensor output. Additional activities may be selected, for example, from a list of possible activities and corresponding activity factors hosted on a website.

Alternative graphical user interfaces may be used to adjust activity factors without first attempting to classify activities. For example, a nested menu structure may be used to allow user to select from all possible activities. The nested structure may include categories, subcategories, etc. For example, a running category may include jogging, running and sprinting subcategories. Some nested menu structures may arrange categories and sub categories so that likely activities are identified first or in other prominent positions. Activities may be identified as likely by considering factors such as a user's history, profile and the activities closest to being identified in step 302 above. Some graphical user interfaces may also allow user to label activities. The use of labels facilitates organizing and searching activities later.

In some embodiment of the invention activities that are part of a menu structure are linked to activity factors. The link may be via a lookup table or other mechanism used to associate activities with activity factors and may be stored on a device worn by a user, a computer device and/or a mobile device. Multiple activities may have the same activity factor and some activities may be assigned a default activity factor.

The graphical user interface shown in FIG. 4 may be presented to a user utilizing a local computer application, accessing a website or using some other device. Portable devices, such as wrist worn devices or mobile phones, may also provide users with the ability to reclassify activities or override default classifications. In some embodiments the form factors of the devices will result in different interfaces and different mechanisms for making the adjustments.

In an embodiment, user 124 may through a worn device i.e., wrist mounted sensor, provide information regarding an activity that the user will engage in or has just completed such as running, walking, or bicycling. A menu may be presented after double tapping an input button, such as button 228 shown in FIG. 2B, or performing some other selection or gesture. Gestures may be sensed by an accelerometer. The menu may be displayed on a display, such as display 234 which is also shown in FIG. 2B. The menu may cycle through various screens in response to a user selecting a button, performing a gesture or providing some other input. In an alternative embodiment, user 124 may enter such information through a user interface screen of computer 100 or a mobile application found on a handheld device such as a mobile phone. The information about the event may be entered prior to the start of the activity or at a much later time and/or date. In some embodiments a user may identify an activity at a device, such as a wrist worn device, and the device may determine when the activity has ended. The device may monitor sensors and determine that an identified activity has ended based on a lack of sensed activity or characteristics of the sensed activity. A user 124 may be prompted to confirm the activity just completed. A sound, vibration, or a display such as a user interface screen may alert a user to confirm information on the activity just completed. The information may include verification that the activity has ended i.e., 5K run has been completed. A prompt may also be used to prompt a user to identify the next activity. The beginning of the next activity will correspond with the ending of the previous activity. When a user does not identify that an activity has ended at a worn device, the user may be prompted to later when synchronizing or analyzing data with a computer device. An activity may be flagged as open ended and a message or menu option may prompt the user to provide an end time.

Figure 5:
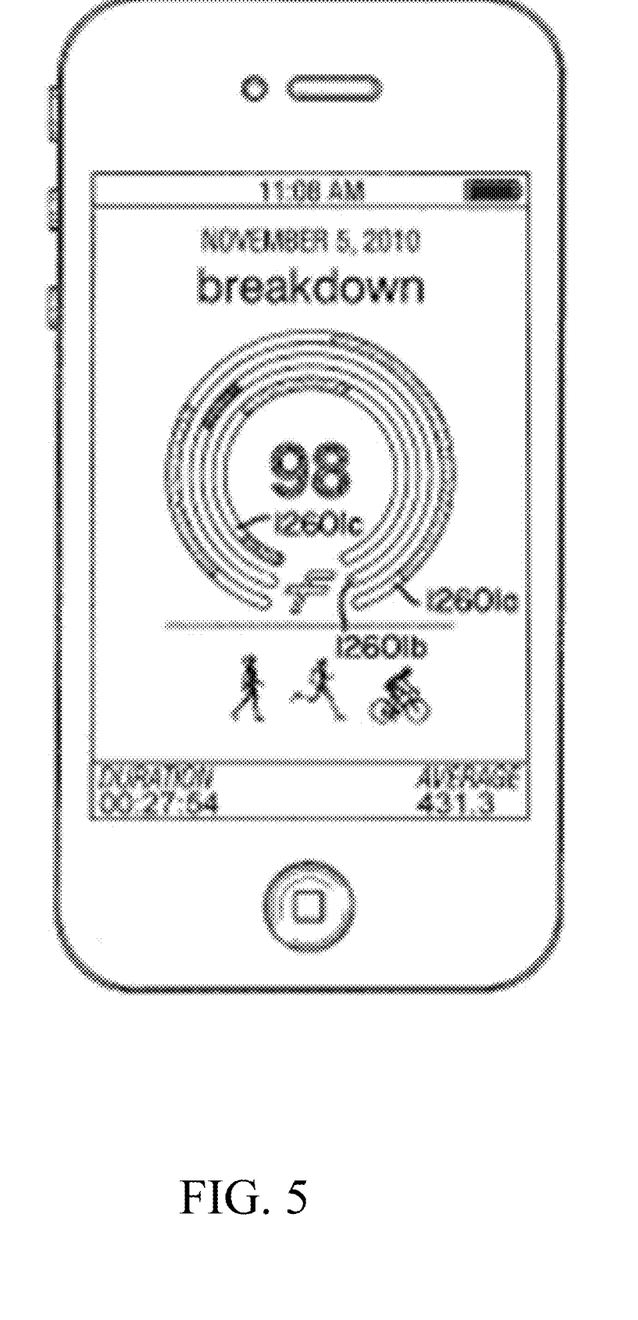
FIG. 5 illustrates an exemplary activity tracking interface in accordance with an embodiment of the invention.

FIG. 5 illustrates an exemplary activity tracking interface in which an activity type may be used to categorize or divide the performed activity in accordance with an aspect of the disclosure. In FIG. 5, for example, each arcuate portion 12601*a*, 12601*b*, and 12601*c* may correspond to a different activity. The portion filled in each of arcuate portions 12601*a*, 12601*b*, and 12601*c* may correspond to a time of day at which the activity was performed. A user such as user 124 may confirm that the activities displayed were performed and/or make any appropriate modifications or edits to the displayed activities.

In one embodiment, based on user confirmation of the activity and associated collected sensor data, a signal template may be generated. The generated template may be used in place of default template for this user for the activity identified. In an alternative embodiment, a default template may be updated based on the received user confirmation.

Conclusion

Providing an activity environment having one or more of the features described herein may provide a user with an experience that will encourage and motivate the user to engage in athletic activities and improve his or her fitness. Users may further communicate through social communities and challenge one another to participate in point challenges.

Aspects of the embodiments have been described in terms of illustrative embodiments thereof. Numerous other embodiments, modifications and variations within the scope and spirit of the appended claims will occur to persons of ordinary skill in the art from a review of this disclosure. For example, one of ordinary skill in the art will appreciate that the steps illustrated in the illustrative figures may be performed in other than the recited order, and that one or more steps illustrated may be optional in accordance with aspects of the embodiments.

What is claimed is:

1. A method comprising:
   receiving, from a sensor system, a first set of data indicating one or more athletic movements performed by a user;
   identifying a default activity template based at least in part on the received first set of data;
   classifying the one or more athletic movements performed by the user as a first activity;
   providing an interface that displays sensor data corresponding to the one or more athletic movements performed by the user, wherein the interface includes a first interface element that allows a user to reclassify captured athletic movements as a different activity type;

receiving, from the sensor system, a second set of data indicating at least one gesture performed by the user, wherein the at least one gesture provides control input indicating a selection of the first interface element;

reclassifying the one or more athletic movements performed by the user as a second activity in response to receiving the second set of data;

determining an activity factor corresponding to the second activity; and at a processor calculating an energy expenditure point value by multiplying the activity factor by a duration of the first activity.

2. The method of claim 1, further comprising generating a customized activity template based at least in part on the received first set of data and the second activity.

3. The method of claim 1, wherein the sensor system comprises an accelerometer.

4. The method of claim 3, wherein classifying the one or more athletic movements further comprises:

associating the first activity with the default activity template.

5. The method of claim 1, wherein the first activity is associated with an activity factor that comprises at least one of: running, walking, and/or bicycling.

6. The method of claim 1, wherein classifying the one or more athletic movements performed by the user as a first activity further comprises:

comparing the received first set of data with sensor data comprising the default activity template.

7. The method of claim 1, wherein the interface is provided on a computer device that does not include the sensor system.

8. The method of claim 1, wherein the interface is provided on a wrist worn device.

9. A method comprising:

receiving, from at least one multiple axis accelerometer, a first set of data indicating athletic movements performed by a user;

identifying a default activity template based at least in part on the received first set of data;

classifying the athletic movements performed by the user as a first activity;

providing an interface that displays the first set of data corresponding to the athletic movements performed by the user, wherein the interface is configured to reclassify captured athletic movements as a plurality of different activity types;

receiving, from the at least one multiple axis accelerometer, a second set of data indicating at least one gesture performed by the user;

reclassifying the athletic movements performed by the user as a second activity in response to receiving control input in accordance with the second set of data;

determining an activity factor corresponding to the second activity; and at a processor calculating an energy expenditure point value by multiplying the activity factor by a duration of the first activity.

10. The method of claim 9, further comprising generating a template based on the athletic movements performed by the user with the at least one multiple axis accelerometer.

11. The method of claim 9, wherein the first activity associated with the activity factor comprises at least one of: running, walking, and/or bicycling.

12. The method of claim 9, wherein the interface is provided on a mobile device that does not include the multiple axis accelerometer.

13. The method of claim 9, wherein the interface is provided on a computer device that does not include the multiple axis accelerometer.

14. The method of claim 9, wherein the interface is provided on a wrist worn device.

15. An apparatus comprising:

a processor; and memory communicatively coupled to the processor and storing executable instructions that when executed, cause the apparatus to:

receive, from a sensor system, a first set of data indicating one or more athletic movements performed by a user;

identify a default activity template based at least in part on the received first set of data;

classify the one or more athletic movements performed by the user as a first activity;

provide an interface that displays the first set of data corresponding to the one or more athletic movements performed by the user;

receiving, from the sensor system, a second set of data indicating at least one gesture performed by the user reclassify the one or more athletic movements performed by the user as a second activity in response to receiving control input selection in accordance with the second set of data;

determine an activity factor corresponding to the second activity; and calculate an energy expenditure point value by multiplying the activity factor by a duration of the first activity.

16. The apparatus of claim 15, wherein the executable instructions, when executed, further cause the apparatus to:

associate the first activity with the default activity template.

17. The apparatus of claim 15, wherein the sensor system comprises at least an accelerometer.

18. The apparatus of claim 17, wherein the accelerometer comprises a multiple axis accelerometer.

19. The apparatus of claim 15, wherein the interface comprises an input button and an array of lights.

20. The apparatus of claim 15, wherein the executable instructions, when executed, further cause the apparatus to:

generate a customized activity template based at least in part on the received first set of data the second activity.

* * * * *